United States Patent [19]

Mueller et al.

[11] Patent Number: 5,415,652
[45] Date of Patent: May 16, 1995

[54] METHOD AND APPARATUS FOR THE TREATMENT OF HARD BIOLOGICAL MATERIAL, SUCH AS HARD DENTAL MATERIAL USING LASERS

[75] Inventors: Gerhard Mueller; Thomas Ertl, both of Berlin, Germany

[73] Assignee: Siemens Aktiengesellschaft, Munich, Germany

[21] Appl. No.: 254,427

[22] Filed: Jun. 6, 1994

Related U.S. Application Data

[63] Continuation of Ser. No. 934,771, Aug. 24, 1992, abandoned.

[30] Foreign Application Priority Data

Aug. 28, 1991 [DE] Germany ............... 41 28 617.0

[51] Int. Cl.$^6$ ........................ A61N 5/06; A61B 17/32
[52] U.S. Cl. ........................ 606/3; 606/16; 606/17; 604/27
[58] Field of Search ........................ 606/14, 15, 16, 17, 606/18; 604/27; 433/29, 215

[56] References Cited

U.S. PATENT DOCUMENTS

| | | |
|---|---|---|
| 3,620,597 | 11/1971 | Schwartz et al. |
| 3,801,825 | 4/1974 | Schwartz et al. |
| 4,019,159 | 4/1977 | Hon et al. ............ 372/34 |
| 4,732,448 | 3/1988 | Goldenberg ............ 606/16 |
| 4,736,743 | 4/1988 | Diakuzono ............ 606/16 |
| 4,785,805 | 11/1988 | Joffe et al. ............ 606/15 |
| 4,808,789 | 2/1989 | Muncheryan |
| 4,819,630 | 4/1989 | Dehart ............ 606/15 |
| 4,826,431 | 5/1989 | Fujimura et al. |
| 4,849,859 | 7/1989 | Nagasawa |
| 4,909,609 | 3/1990 | McDowell |
| 5,020,995 | 6/1991 | Levy ............ 433/215 |
| 5,047,638 | 9/1991 | Cameron et al. ............ 250/330 |
| 5,118,293 | 6/1992 | Levy |
| 5,123,845 | 6/1992 | Vassiliadis et al. ............ 433/215 |
| 5,128,948 | 7/1992 | Papuchon et al. ............ 372/75 |
| 5,139,494 | 8/1992 | Freiberg ............ 606/16 |
| 5,151,029 | 9/1992 | Levy |

(List continued on next page.)

FOREIGN PATENT DOCUMENTS

| | | |
|---|---|---|
| 0073617 | 3/1983 | European Pat. Off. |
| 3444824 | 9/1987 | Germany |
| 3800555 | 7/1989 | Germany |
| 3841503 | 6/1990 | Germany |

(List continued on next page.)

OTHER PUBLICATIONS

"Wissensspericher Lasertechnik," pp. 78–79 and 492–493.

"Electrooptically Q-Switched 2.79 $\mu$m YSGG:Cr:Er Laser with an Intracavity Polarizer," Breguet et al., IEEE J. Quant. Electr., vol. 27, No., Feb. 1991, pp. 274–276.

"Suppression of Laser Spiking by Intracavity Second Harmonic Generation," Jeys, Applied Optics, vol. 30, No. 9, Mar. 20, 1991, pp. 1011–1013.

"Comparison of YAG:Er and YALO$_3$:Er Laser Crystals Emitting Near 2.9 $\mu$m," Wüthrich et al., J. Appl. Phys. vol. 68, No. 11, Dec. 1, 1990, pp. 5467–5471.

(List continued on next page.)

*Primary Examiner*—Peter A. Aschenbrenner
*Assistant Examiner*—Sonya C. Harris
*Attorney, Agent, or Firm*—Hill, Steadman & Simpson

[57] ABSTRACT

A method and apparatus for the ablation of hard biological material, such hard dental material, using a rapidly pulsed laser employ a crystal disposed in the propagation path of the laser radiation, the crystal being disposed at the laser output and serving as an interface with an optical conductor which conveys the laser radiation to the treatment site. The crystal smooths the time/intensity characteristics of the pulsed laser radiation to the extent that transmission to the treatment site using optical wave guides is possible. Additional protective features are provided to prevent the ablated biological material to destroy the exposed optical end surfaces of the treatment applicator. Additional design features improve the ergonomic efficiency of the handpiece and its ability to be sterilized.

19 Claims, 9 Drawing Sheets

U.S. PATENT DOCUMENTS

| | | |
|---|---|---|
| 5,151,031 | 9/1992 | Levy . |
| 5,169,318 | 12/1992 | Levy . |
| 5,171,150 | 12/1992 | Levy . |
| 5,188,532 | 2/1993 | Levy . |
| 5,192,279 | 3/1993 | Samuels et al. ............... 128/664 |
| 5,194,005 | 3/1993 | Levy . |
| 5,199,870 | 4/1993 | Steiner et al. ............... 433/215 |

FOREIGN PATENT DOCUMENTS

| | | |
|---|---|---|
| 3911871 | 10/1990 | Germany . |
| 4030734 | 4/1991 | Germany . |
| 3911853 | 12/1991 | Germany . |
| 878137 | 8/1988 | U.S.S.R. . |

OTHER PUBLICATIONS

"Temperature Sensitivity of Phase-Matched Second Harmonic Generation in $LiIO_3$," Webb et al., J. Quant. Electr., vol. 26, No. 8, Aug. 1990, pp. 1394–1398.

"Non-Linear Population Processes of $Er^{3+}$ Laser Levels in Chromium–Doped Garnet Crystals," Noginov et al., Optical and Quant. Electr., vol. 22, 1990, pp. S61–S74.

"$AgGaS_2$ Infrared Parametric Oscillator," Fan et al., Appl. Phys. Lett. vol. 45, No. 4, Aug. 15, 1984, pp. 313–315.

"Infrared Radiation Tunable from 5.5 to 18.3 $\mu m$ Generated by Mixing in $AgGaS_2$," Seymour et al., Appl. Phys. Lett., vol. 29, No. 11, Dec. 1, 1976, pp. 705–707.

METHOD AND APPARATUS FOR THE TREATMENT OF HARD BIOLOGICAL MATERIAL, SUCH AS HARD DENTAL MATERIAL USING LASERS

This is a continuation of application Ser. No. 07/934,771, filed Aug. 24, 1992, now abandoned.

BACKGROUND OF THE INVENTION

1. Field of the Invention

The present invention is directed to a laser-based method and apparatus for the treatment of hard biological material, such as the ablation and removal of hard dental material.

2. Description of the Prior Art

Processes and devices employing a pulsed laser for removing hard biological material, such as hard dental material are described, for example, in German OS 4 030 734 and OS 3 911 871. In OS 4 030 734, a particular technique, and various types of equipment for implementing the technique, are described for treating carious teeth and for conducting root canal repairs. The devices described therein, in general, include a pulsed laser, a fiber optic transmission system, and a fiber optic laser-transmitting handpiece with interchangeable therapy heads. The source of the radiation is a pulsed alexandrite solid-state laser, operating in the wavelength range between 720 and 860 nm. By the addition of an appropriate optical module, it is possible to double the frequency, and therefore attain an operating range between 360 and 430 nm. In one embodiment of this known system, the laser beam is emitted from the removable head as a "free" beam, that is, the focus lies outside the emission plane. In another embodiment, the emission point is at the end of a light waveguide which is located in the therapy head. The laser beam is emitted as a dispersing beam in this embodiment. This embodiment is designed specifically for the preparation of root canals. The coupling into and out of light guides is generally accomplished using spherical lenses. At the point of termination, the face of both the handpiece and the therapy head contain a window made of compressed quartz glass having anti-reflective properties. This prevents dust and dirt from entering the individual components of the equipment.

In OS 39 11 871, a process is described for the removal of dental material using a pulsed infrared laser. In this known method, the dental material is covered with a thin film consisting of a fluid which absorbs laser radiation, either before or during the irradiation process. By this technique, the danger of damage to the surrounding healthy tissue is reduced, while not interfering with the efficiency of the removal of dental material. The fluid is applied intermittently, i.e., during the pauses between the respective laser pulses.

It is generally known that, using a pulsed laser system, the individual pulses of the laser radiation may exceed the threshold of critical energy concentration (which varies by material), so that biological material can be removed without creating a significantly increased temperature in the areas peripheral to the treatment location. To achieve these results, however, extremely short light pulses (on the order of nanoseconds) must be used, and the thickness of the biological material removed by this method is between 10 and 50 microns. To reach worthwhile rates of material removal, given such a tiny thickness per individual light pulse, it is necessary to increase the repetition rate of the laser pulses. Because hard biological material has a limited heat transfer capacity, however, increasing the repetition rate of the pulses rapidly leads to an accumulation of heat around the zone of removal, and hence leads to thermal damage of the areas peripheral to the treatment area. To reduce the level of thermal damage resulting from the use of laser systems wherein the laser radiation is not significantly absorbed by naturally-present water or air, various types of cooling equipment are known which generate a continuous jet of water or a continuous flow of air to the treatment site.

It is known that transmitting high intensity laser radiation through optical fibers can cause a photohydraulic phenomenon at the treatment site, which causes the biological material which has been ablated by the action of the laser pulses to impinge on the exit face of the light guide, thereby resulting in the destruction of the light guide fibers. This, in turn, requires that the treatment be terminated. In an effort to avoid this problem, the transmission of such high intensity light levels is usually accomplished by using movable arms which incorporate mirrors. Such a transmission method is disclosed, for example, in the German OS 39 11 853. This document shows an opto-mechanical endpiece for one such mirror arm for an Er:YAG laser. This arrangement permits the transmission of pulsed laser radiation,, however, such mirror systems have the disadvantage that any error in the assembly, or in the direction of the output of the laser radiation, is increased by a factor of two with each mirror present in the apparatus. Therefore, any deviations in the coaxiality of the system resulting from misalignments at the optical interface locations, or dynamic variations in the output direction of the laser radiation, or its angle of dispersion, are multiplied by two for each point at which the light changes direction. Such mirror systems are, therefore, extremely difficult to adjust. Moreover, the cost of manufacturing the mechanical parts with the necessary precision is, as a result, very high. Additionally, such mirror systems are freely movable only within limits, because considerable force is required to articulate each point of directional change, and any two points cannot always be connected with each other along the shortest path. Although it is theoretically possible to transmit optical radiation using light waveguides, the ability to transmit high intensity short laser pulses, under conditions as described above, is limited by the technical capabilities of the material currently available for the manufacture of optical fibers.

SUMMARY OF THE INVENTION

It is an object of the present invention to provide a method and apparatus for treating hard biological substances, such as bones or teeth, (as an alternative to the conventional dental procedures of drilling or grinding) without generating thermal damage in areas peripheral to the treatment area, those peripheral areas being at a greater depth than the optical depth of penetration of the laser radiation.

It is a further object of the present invention to provide such a method and apparatus wherein the rate of removal of the biological material is, in terms of volume removable per unit of time, comparable to rates achievable using conventional procedures.

It is another object of the present invention to provide such a method and apparatus which can be used not only in a laboratory environment, but also for human treatment, in which case the opto-mechanical endpieces of the apparatus must be capable of being easily sterilized.

Another object of the present invention is to provide a method and apparatus wherein the opto-mechanical endpiece of the equipment is designed to be hand-held and is freely movable in all directions.

The invention is based on the perception that, surprisingly, the threshold for volume destruction of optical fibers is significantly higher than the threshold at which surface destruction takes place under bombardment with high-intensity laser light. The surface destruction threshold increases approximately in proportion to the square root of the pulse length. This means that, in the borderline case of a laser which is continuously irradiating, the surface and volume destruction thresholds move closer together. In order to meet the criterion of having the smallest possible amount of damage in the areas peripheral to the treatment area, only lasers having emission wavelengths of either less than 400 nanometers, or greater than 1.1 microns, can be used. Taking the further criterion into account, that the removal rates must be comparable to those achievable using conventional systems, the applicable lasers are only those with pulse lengths which lie between approximately 0.5 and 500 microseconds. Considering the absorption curve of hard dental materials or bone, working wavelengths in the respective ranges of 200 through 400 nm, 1.3 through 3 microns, and 9.0 through 11 microns can be used. In a preferred embodiment, a solid-state laser is used having an emission wavelength of 2.78 microns. Ideally, this would be a YSGG crystal laser (Yttrium Scandium Gadolinium Garnet) with Cr-Er doping. Alternatively, good results can be obtained using an Er:YAG laser which emits radiation at a wavelength of 2.94 microns. Lasers which emit radiation between these two wavelengths (i.e., between 2.78 microns and 2.94 microns) are preferentially acceptable. The laser is used with media which achieves smoothing of the time intensity characteristics of the laser pulses, so that transmission of those pulses using optical waveguides is viable.

It is surprising that the ablation which takes place at the treatment site causes the absorption maximum of the target material to dynamically shift to shorter wavelengths, and that this occurs even during the time when a pulse laser is in actual operation. In combination with the design measures described below, this surprising revelation can be used to achieve a system for treating hard biological material wherein the light can be transmitted to the treatment site by an optical waveguide, without damaging the optical waveguide to an extent requiring the treatment to be stopped. In the specific example of water-containing hard dental material (hydroxylapatite), its absorption maximum shifts from around 3 microns to approximately 2.8 microns. Thus, when the preferred wavelength is used, the process "optimizes" itself during the course of each individual pulse.

DESCRIPTION OF THE PREFERRED EMBODIMENTS

Figure 1:
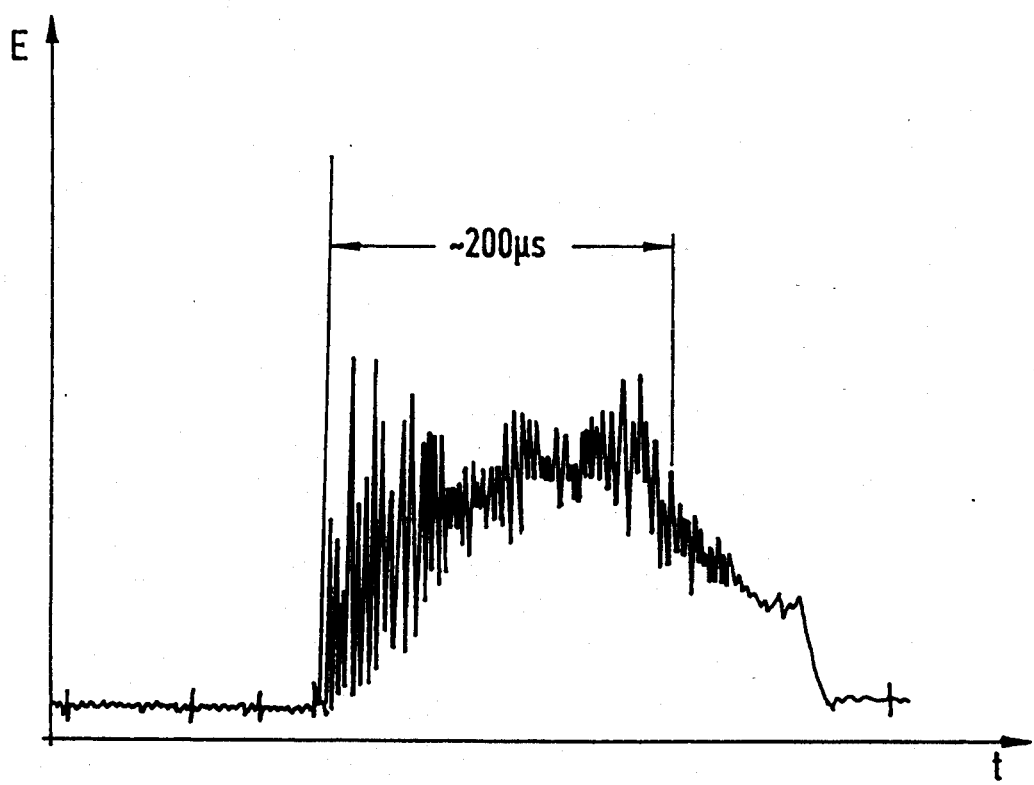
FIG. 1 is a graph of the emission performance over time of a pulsed solid-state laser.

The emission performance over time of a conventionally operated pulsed solid-state laser is shown in FIG. 1. As a result of the spikes, which are greatly amplified compared to the average energy level, very high concentrations of energy will be present at the surface of the optical fibers, which are used to conduct the laser light, at the point of interface with the laser radiation. Even when the levels of energy concentration are too low to cause actual volume destruction of the fibers, the fiber surface is nonetheless frequently destroyed at the time of coupling of the radiation to the light waveguide, and the system will therefore malfunction.

Figure 2:
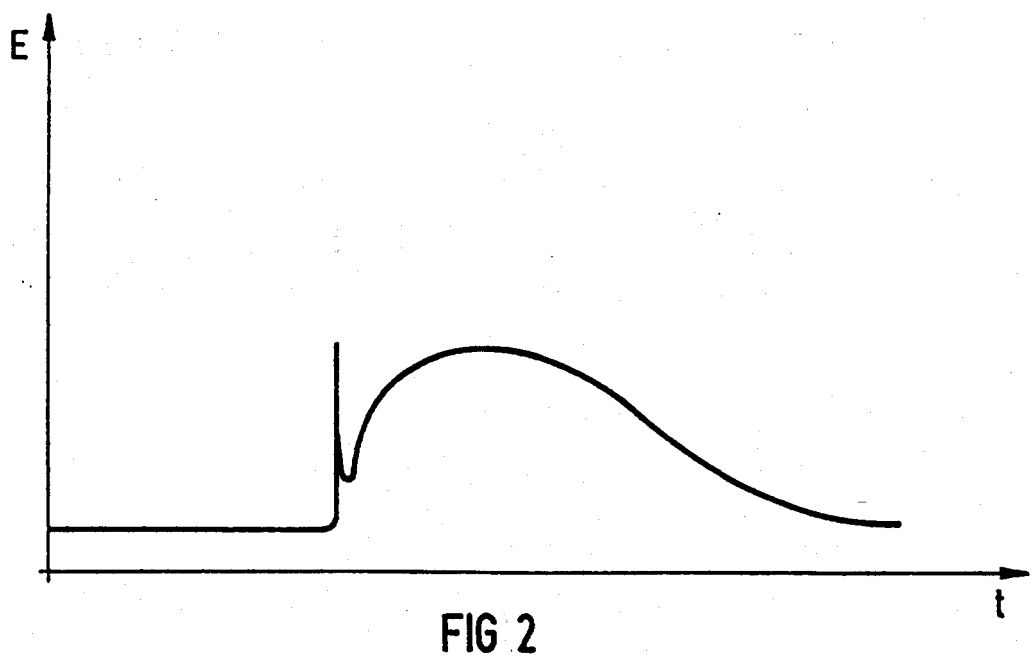
FIG. 2 is a graph of the emission characteristics achieved in accordance with the principles of the present invention, which are ideal for transmitting high energy pulses.

Ideal emission characteristics for transmitting high energy pulses, as are achieved in accordance with the principles of the present invention, are shown in FIG. 2. In accordance with the invention, the technical problem of easily transmitting the light from a pulsed laser using optical fibers is solved by placing a medium in the region of highest laser beam density which "smooths" the intensity characteristics of the beam with respect to time. In a preferred embodiment, this medium is a crystal with non-linear optical characteristics (which will generate harmonics at several times the base frequency), which is placed in the center of the laser beam, either inside or outside of the laser resonator (cavity). Above certain threshold values of energy concentration, the crystal generates the harmonics of the base wavelengths with a high degree of efficiency. The crystal may consist, for example, of lithium-iodate, lithium beta borate, lithium niobate, niobium beta borate, barium beta borate or silver gallium sulfide. In combination with further design steps with respect to the optics, as described below, or by way adding optical elements in the propagation path of the beam, the region of highest beam density attains such a level of concentration for the chaotic emission pulses that, above a given energy concentration level corresponding to the average value of a pulse, the intensity spikes are doubled in frequency. Such intensity spikes are then no longer amplified.

Figure 3:
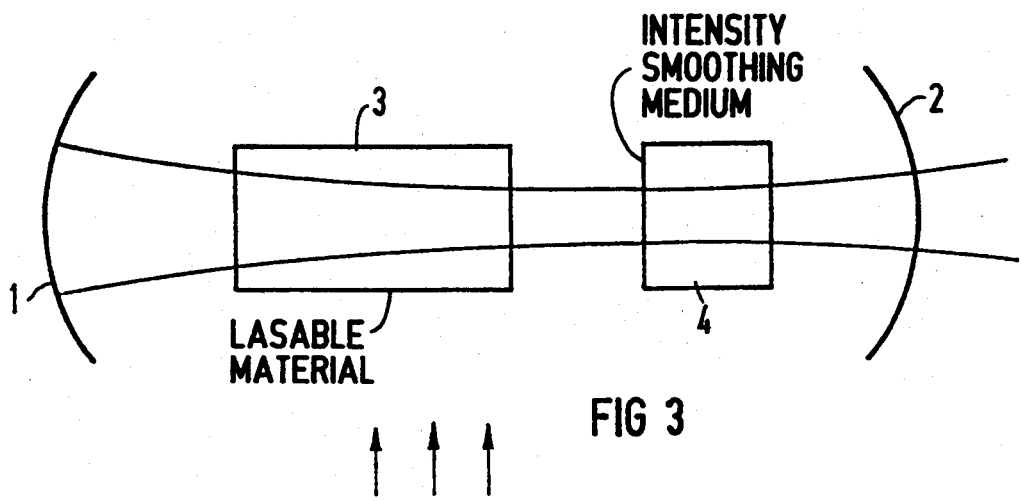
FIG. 3 is a schematic representation of a laser resonator with an intensity smoothing element disposed inside the resonator, in accordance with the principles of the present invention.
Figure 4:
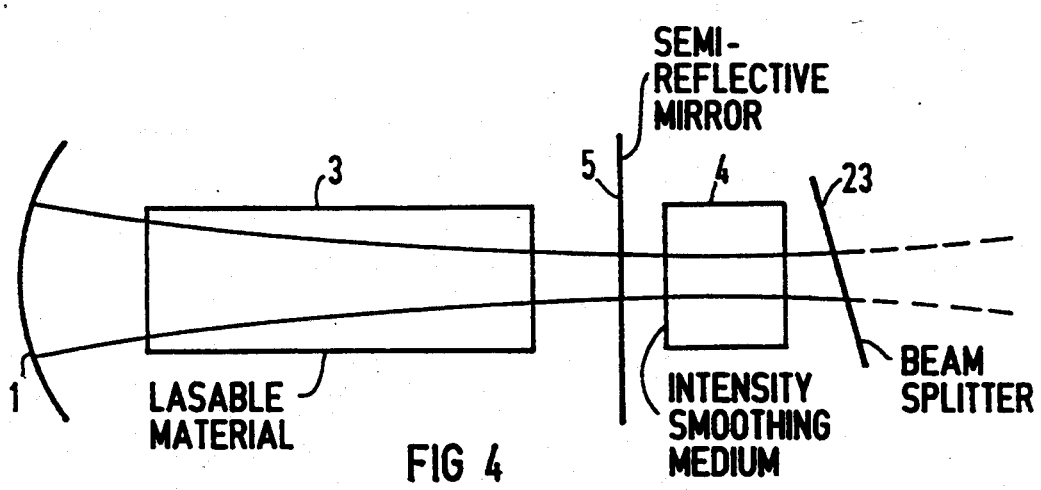
FIG. 4 is a schematic representation of a laser resonator with an intensity smoothing element disposed outside of the resonator, in accordance with the principles of the present invention.

Two highly schematic embodiments of a laser with the aforementioned intensity smoothing medium, in accordance with the principles of the present invention, are shown in FIGS. 3 and 4. In the embodiment of FIG. 3, the laser resonator has two confocal (convex curved) mirrors 1 and 2, between which a lasable substance 3 is disposed. The lasable substance 3 can be a gas, fluid, or a solid such as a semiconductor. The intensity smoothing medium 4, such as a crystal, is disposed inside the resonator. The intensity smoothing medium 4 has the characteristics as described above. Inside the resonator, the harmonics are not further amplified, because of the frequency-selective amplification characteristics of the lasable medium 3. In the embodiment of FIG. 3, the impulse spikes are in fact clipped, although the base wavelength continues to be amplified. An arrangement as shown in FIG. 3, with the medium 4 disposed within the resonator, causes the lowest possible losses.

It is also possible, however, to dispose the medium 4 outside of the resonator, as shown in FIG. 4. In the embodiment of FIG. 4, the resonator has a semi-reflective plane mirror 5 disposed at one end thereof. With this arrangement, the conditions for generating the harmonics can, with good results, be more easily selected and adjusted. The embodiment of FIG. 4 also includes a dichroic beam splitter 23, which reflects the intensity spikes of the frequency-doubled laser pulses, so that those spikes are not present in the output beam, which passes through the beam splitter 23. With such a smoothed intensity profile, using an Er:YSGG pulsed laser, laser pulse energy levels of more than 500 mJ, at impulse widths of around 180 microseconds, can be transmitted using the latest available optical fibers. It will be understood that any other non-linear optical mechanism can be used to clip the impulse spikes, without departing from the inventive concept disclosed herein, in order to achieve an optimal interface of the high-intensity light pulses with the light transmitting medium. Another example of such a mechanism is a two photon absorber.

Figure 5:
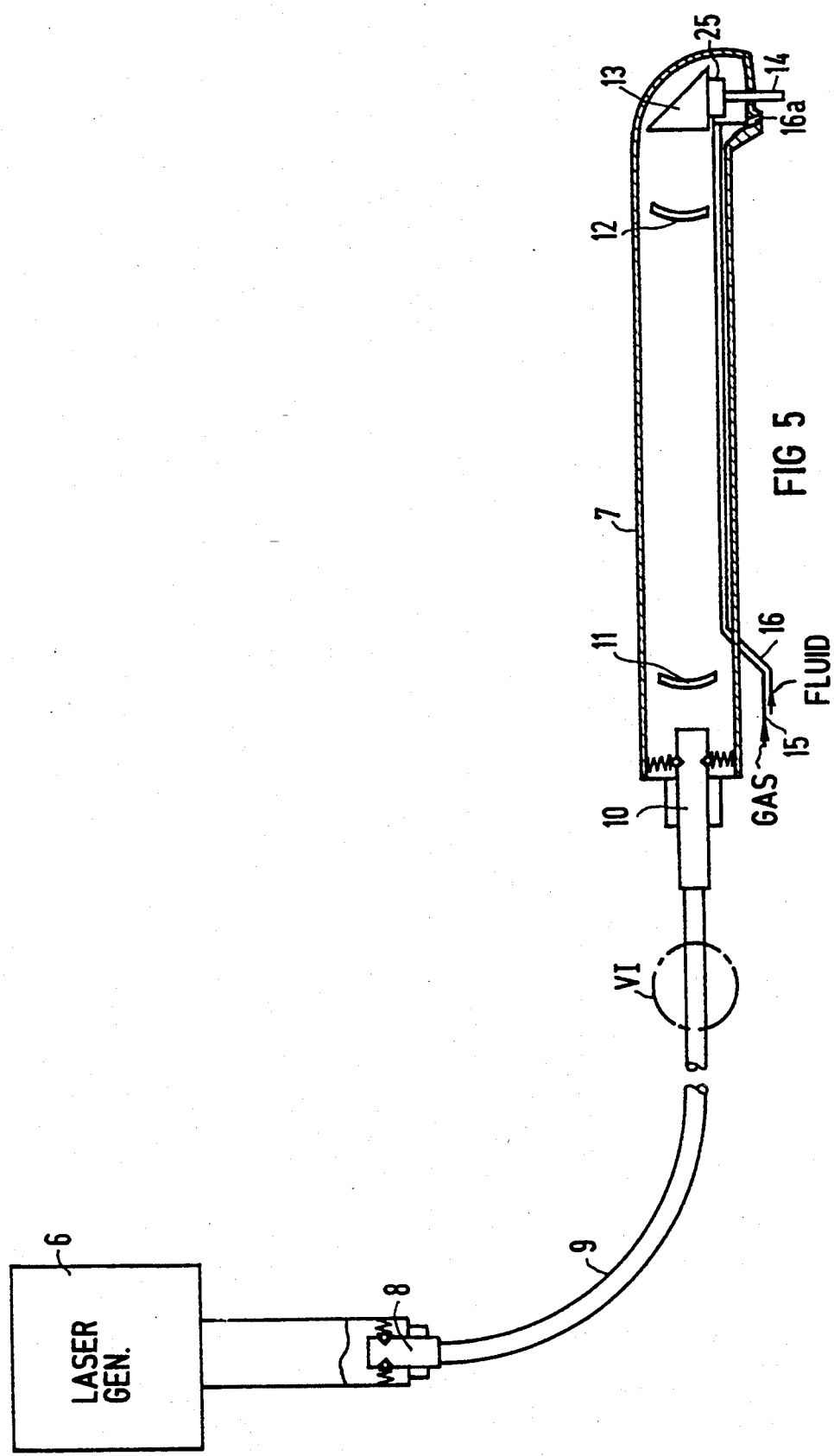
FIG. 5 is a side view, partly in section, of an apparatus for treating hard biological material constructed in accordance with the principles of the present invention, in the form of a dental instrument.

Details of a practical embodiment of the invention are shown in FIG. 5 in the form of a dental apparatus. In the apparatus of FIG. 5, laser light is generated by a laser generator, generally referenced 6, constructed and operating either as shown in FIG. 3 or FIG. 4. This light is supplied to a dental handpiece 7. The light output beam at the resonator of laser generator 6 is directed to the center of a first twist connector 8, which transmits the light via an optical interface, which is not further described. The light then passes through a flexible light waveguide tube 9 to a second twist connector 10, which is in turn connected to the handpiece 7. The handpiece 7 can thus easily be removed from the end of the waveguide tube 9.

From the second twist connector 10, the laser light is transmitted as a "free" beam via optical mirrors and prisms 11, 12, and 13, until eventually reaching an applicator endpiece 14, serving as the treatment tool.

Figure 6:
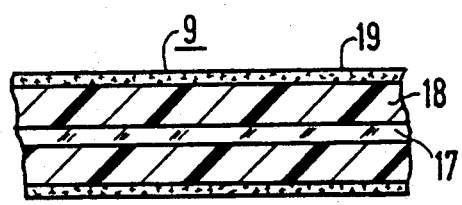
FIG. 6 is a side sectional view of a portion of the light waveguide tube in the apparatus of FIG. 5.

Two conduits 15 and 16, described in greater detail below, are respectively used to carry gas (preferably air) and a liquid (preferably water) to the treatment end of the handpiece 7. The gas conduit 15 is connected at one end to a gas container 25, in a manner described in detail below and is connected at its other end to the liquid conduit 16 via a three-way connector. The gas and liquid are mixed to create an aerosol, and the output nozzle 16a at the end of the liquid conduit 16 is directed toward the treatment area such that the aerosol is sprayed directly onto the area being treated by the laser radiation, and not onto the surrounding area. A section, designated VI in FIG. 5, of the light waveguide tube 9 is shown in enlarged sectional view in FIG. 6. As can be seen in FIG. 6, the optically transmissive material 17 is centrically arranged and wrapped by an jacket 18 consisting of elastomeric material. The light conducting material 17 is preferably zirconium fluoride glass and may be arranged to form a light waveguide consisting of either of a single fiber, or in the form of a multiple fiber arrangement (fiber bundle). This material is relatively flexible, but is still sensitive to torsion, and it is therefore important to insulate the material 17 from torsion forces, or to minimize their effect, for which reason the elastic jacket 18 is used. The viscoelastic properties of the jacket 18 insure that shear or torsion forces are adequately distributed over the boundary surface. Preferably silicon rubber is used for the jacket 18. An outside jacket 19 surrounds the jacket 18. The outer jacket 19 has some degree of flexibility, however, is protected against torsion by a fabric or mesh woven into the jacket 19.

As noted above, at each end of the waveguide tube 9 are respective twist connectors 8 and 10. The twist connectors 8 and 10 are constructed so they can freely turn around the longitudinal axis of the waveguide tube 9, while still connected to the corresponding receptacle, either at the laser side or the applicator side of the waveguide tube 9.

The practical embodiment shown in FIG. 5 employs the aforementioned design criteria to reduce the probability of surface destruction of the ends of the light conducting material 17 and meets the required transmission characteristics for Er:YSGG or Er:YAG laser radiation. The additional requirement of achieving an easily sterilizable optomechanical endpiece is met as follows. The pulsed radiation from the laser generator 6 emitted from the light conducting material 17 in the waveguide tube 9 is passed through the rotary quick connector 10 to the handpiece 7 which has a hollow interior. The handpiece 7 can be separated from the waveguide tube 9 for the purpose of sterilization. The ability to be sterilized is achieved by using only a few optical components, which are not permanently attached together.

FIGS. 5 and 7 through 12 show various embodiments for passing the laser radiation through the interior of the handpiece 7 to the appropriate optical elements disposed at the applicator endpiece 14. All of the embodiments of the handpieces 7 shown in the drawing have the advantage of a removable applicator endpiece. This applicator endpiece can either be supplied in sterile packaging, or may itself be sterilized.

Figure 16:
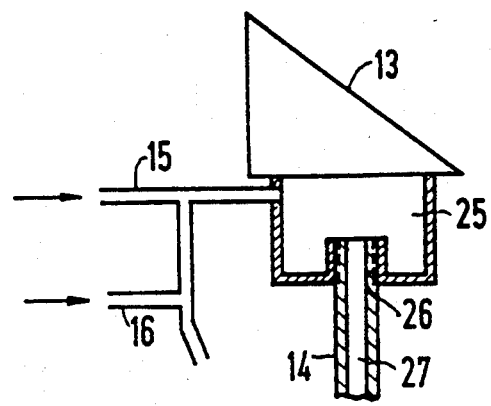
FIG. 16 is an enlarged side sectional view of the treatment end of the handpiece shown in FIG. 5.
Figure 7:
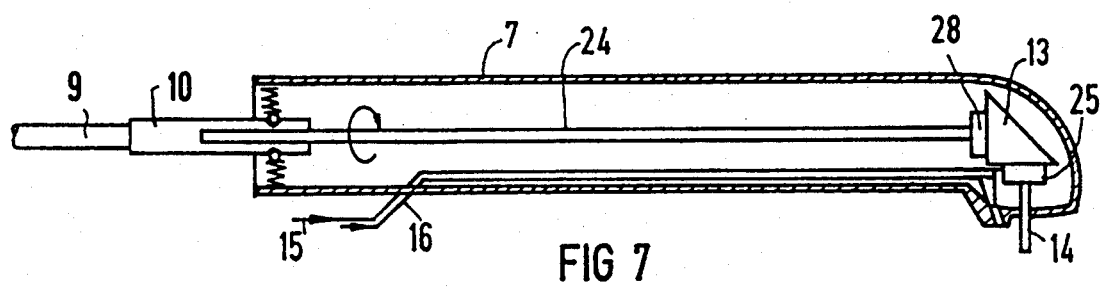
FIG. 7 is a side sectional view of the dental handpiece in a further embodiment for transmitting the laser light to the treatment end of the handpiece.
Figure 8:
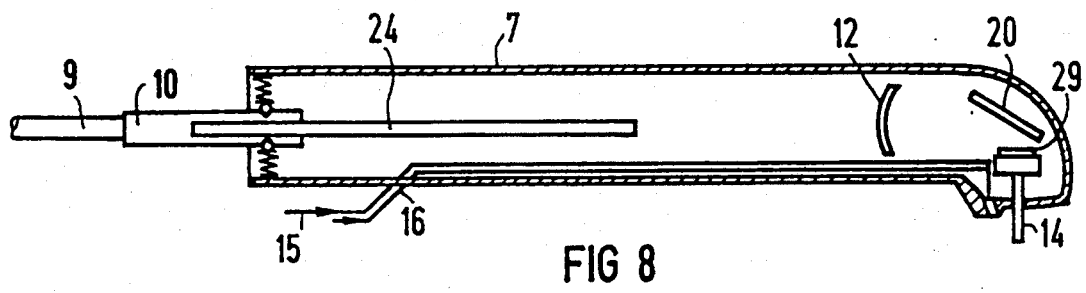
FIG. 8 is a side sectional view of the dental handpiece in another embodiment for transmitting the laser light to the treatment end of the handpiece, using a flat mirror.
Figure 9:
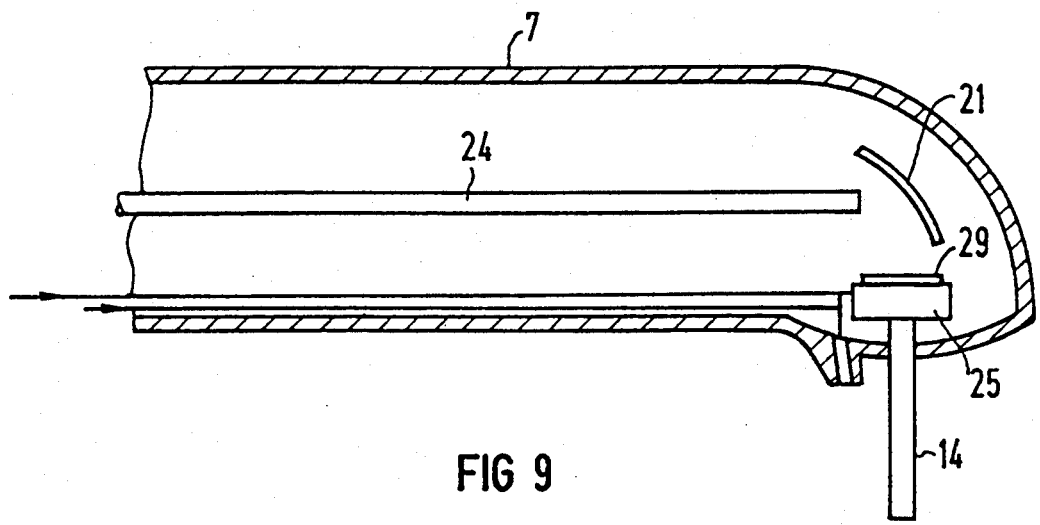
FIG. 9 is an enlarged side sectional view of the treatment end of a further embodiment of a dental handpiece, employing a curved mirror.
Figure 10:
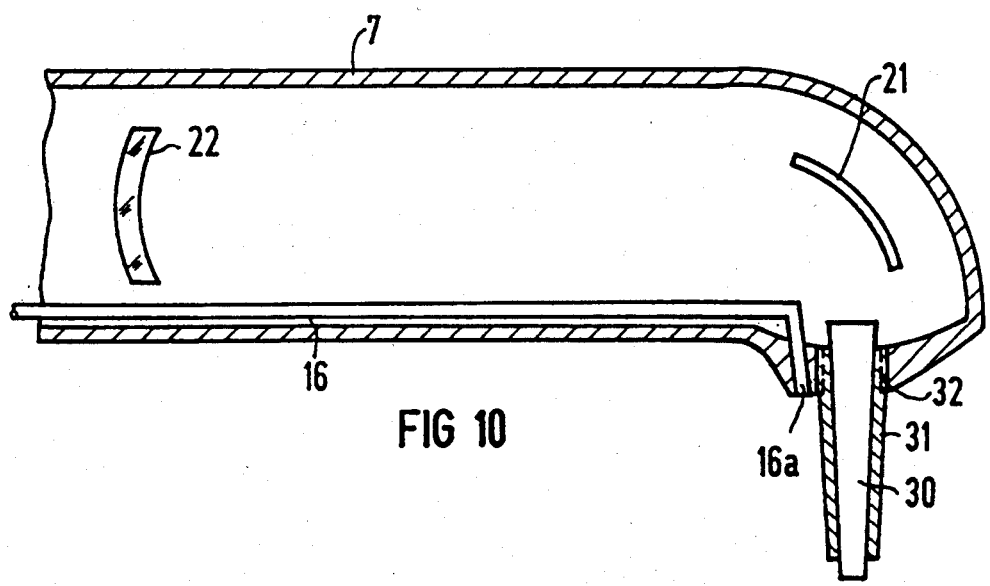
FIG. 10 is an enlarged side sectional view of the treatment end of a dental handpiece in a further embodiment also using a curved mirror, with a different type of treatment tip.
Figure 11:
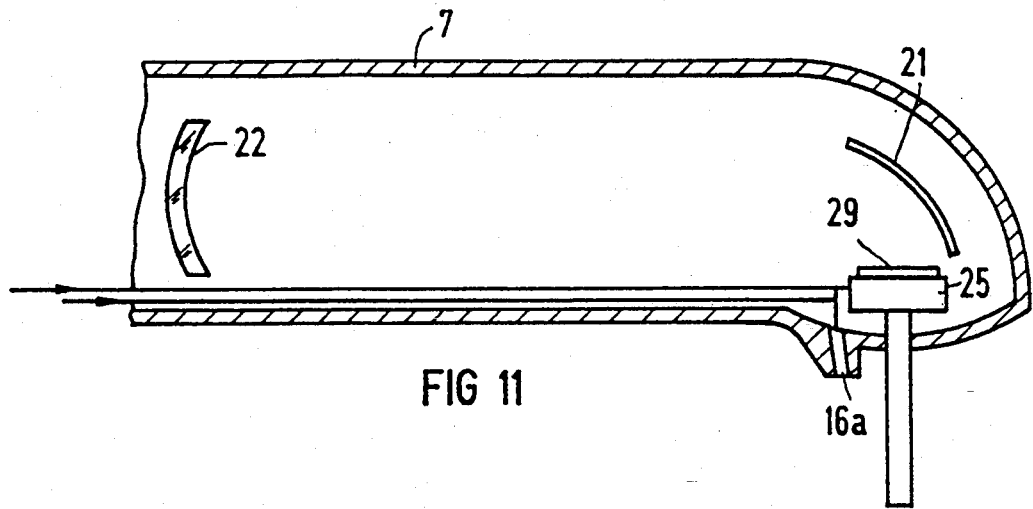
FIG. 11 is an enlarged side sectional view of the treatment end of a dental handpiece, in a further embodiment employing a curved mirror.
Figure 12:
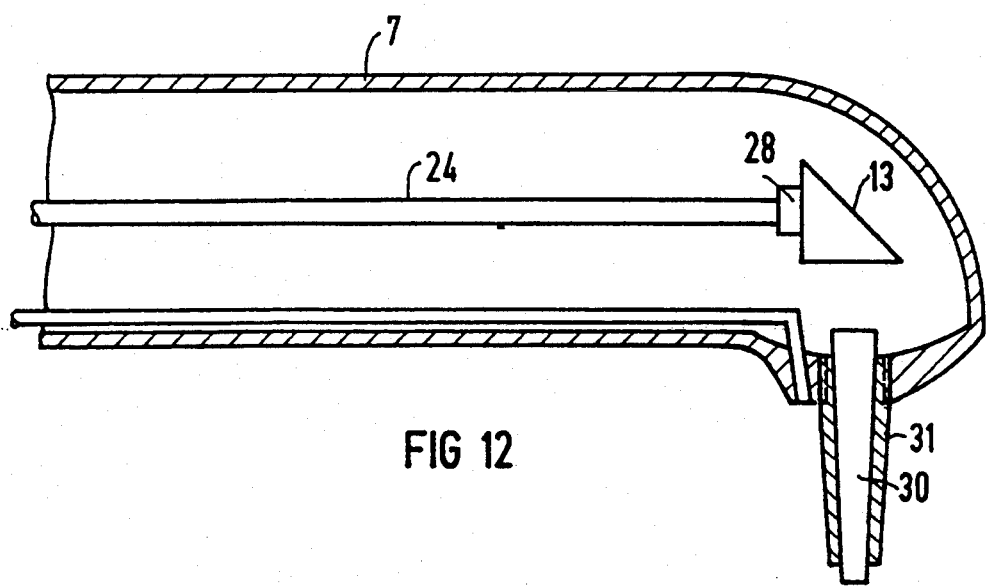
FIG. 12 is an enlarged side sectional view of the treatment end of a dental handpiece in a further embodiment employing a prism with a treatment tip of the type shown in FIG. 10.

In the embodiment of FIG. 5, the laser light is transmitted via two conjugated coaxial imaging lenses 11 and 12. The lenses 11 and 12 are preferably meniscus lenses consisting of sapphire. An image of the output aperture of the light conducting material 17 is thus incident on a input face (surface) of a prism 13, which changes the propagation direction of the laser light by approximately 90° and passes the laser light to the entry aperture of the application endpiece 14. The applicator endpiece 14 or, briefly "applicator" is in the form of a hollow guide. The prism 13 is placed in the propagation path of the lenses 11 and 12 such that total reflection of the laser radiation occurs on the hypothenuse surface of the prism. This allows the beam to be displaced by 90°. As shown in greater detail in FIG. 16, the prism 13 is seated on a gas container 25. Gas (preferably air) is supplied to this container 25 through the gas conduit 15, in accordance with the invention. The gas container 25 has a screw connector 26 which permits different applicator endpieces 14 of varying lengths and opening types to be interchanged with one another.

A portion of the compressed gas used to form the aerosol is diverted to the gas container 25, and is expelled therefrom through a channel 27 in the applicator 14. The gas container 25 achieves a uniform pressure distribution of the gas flow through the channel 27, creating a laminar flow at a ratio of at least 1:10 between the inner diameter and the length of the flow capillaries. Due to the aforementioned photohydraulic phenomenon associated with the particles of biological material which have been ablated by the action of the pulsed laser, such particles would normally tend to be directed back toward the source of the pulsed laser radiation. In accordance with the principles of the present invention, however, these particles are not permitted to reach the optical surfaces of any of the beam direction-changing elements 13, 20, (FIGS. 8, 12) or 21, (FIGS. 9, 10, 11) but are instead expelled to the side by the gas flow through the channel 27. As a result, the action of the gas dynamically protects the sensitive surfaces of the applicator endpiece 14, as well as those of the other components in the handpiece 7, from being damaged by the products of the ablation process. If a gas having a higher refractive index than air is used, the gas itself can have the ability to transmit light, including the laser radiation over a short distance at the end of the hollow applicator endpiece 14. This permits the operator to work in a non-tactile mode, and also affords access for the aerosol cleansing medium.

In a preferred embodiment, interchangeable applicator endpiece 14 is a capillary having a gold-plated interior, which can be removed and exchanged similar to drill bits by a dentist.

The embodiments of FIGS. 7 and 8 include a stiff metal jacket 24, surrounding an extension of the light conducting material 17 from the waveguide tube 9. The stiff metal jacket 24 is mechanically attached at one end to the twist connector 10, and supports the light conducting material 17 in the interior of the handpiece 7. The jacket 24, and the light conducting material 17 therein, terminate close to the beam direction-changing element in the interior of the handpiece 7. As shown in FIG. 7, this may be an optical prism 13 or, as in FIG. 8, a direction-changing mirror 20. To avoid reflection losses at the face of the prism 13, it is preferable to introduce immersion fluid between the end surface of the light conducting material 17 and the direction-changing element. In the embodiment of FIG. 7, this immersion fluid is contained in a capsule 28 in which the end of the metal jacket 24 is disposed. If the light conducting material 17 is in the form of fibers having a suitably small numerical aperture (such as smaller than 0.2), the emitted radiation can be passed directly via the direction-changing element into the interchangeable hollow guide forming the application tip 14.

As shown in FIG. 8, the direction-changing mirror 20 is a plane mirror. In the event that the numerical aperture of the light conducting material 17 is too large to permit the laser radiation to be completely directed into the hollow guide (taking the geometrical distances into account), an angular or curved mirror 21 may be used instead of the planar mirror 20. Such an arrangement is shown in FIG. 9. The mirror 21 causes the radiation to converge in such a manner as to correspond with the entry aperture of the hollow guide in the application tip 14. In this embodiment, the gas container 25 is closed by an optically transmissive window 29, which also facilitates the easy replacement of the application tip 14. Preferably the optically transmissive window 29 is a thin mica pane.

In a further embodiment as shown in FIG. 10, the optics include a lens 22, preferably a meniscus lens, in combination with an toroidal mirror 21. In this embodiment, the laser radiation is directed into a conical sapphire tip 30. The tip 30 is housed in a metal cone 31 to protect it from dirt. The metal cone 31 is held in place at the application end of the handpiece 7 by a screw thread, and can easily be removed and replaced. Because of its hardness and good optical transparency, sapphire is suitable for transmitting the usable wavelengths and is unlikely to be significantly damaged by the particles which are directed back toward it at the distal end due to the aforementioned photohydraulic phenomenon. If, however, damage should occur, the tip 30 can be easily removed and replaced, as is commonly undertaken by a dentist for various drill bits.

The optics combination of a meniscus lens 22 and an angular mirror 21, as shown in FIG. 10, can also be used with dynamic gas protection, as shown in FIG. 9. This combination of embodiments is shown in FIG. 11. Moreover, using a sapphire applicator tip 30, it is also possible to employ the light waveguide material 17 protected by the metal jacket 24, extending directly to the direction-changing element, instead of the reflecting and focusing optics. Such an embodiment employing a prism 13 as the direction-changing element is shown in FIG. 12, however, it will be understood that an angular mirror, such as the mirror 21 can be used in the embodiment of FIG. 12 instead of the prism 13.

In the removal of hard biological material, such as bone or dental material, the operating zone of the laser radiation should have aerosol applied thereto intermittently, in accordance with the principles of the invention. The aerosol drops are carried away as part of the removal process, but a portion of the aerosol drops will be vaporized by the heat, and thus function as heat extractors, so that it is possible to operate at laser pulse repetition rates as high as 15 hertz without the thermally-damaged peripheral zone being any larger than that, for example, arising with the use of an air-powered drill.

It is surprising to find that no loss in efficiency occurs, provided a given ratio between air and liquid is maintained, and the liquid volume is adjusted in accordance with the pulse energy and rate of repetition of the laser pulses. A significantly increased level of ablation quality is also achieved.

These measures make possible, for the first time, the ablation of hard tissue with a high degree of efficiency from an exact location point, while maintaining close temperature tolerances (less than 5° K temperature increase). The apparatus connections for achieving the above method results are shown in FIGS. 13 through 15.

Figure 13:
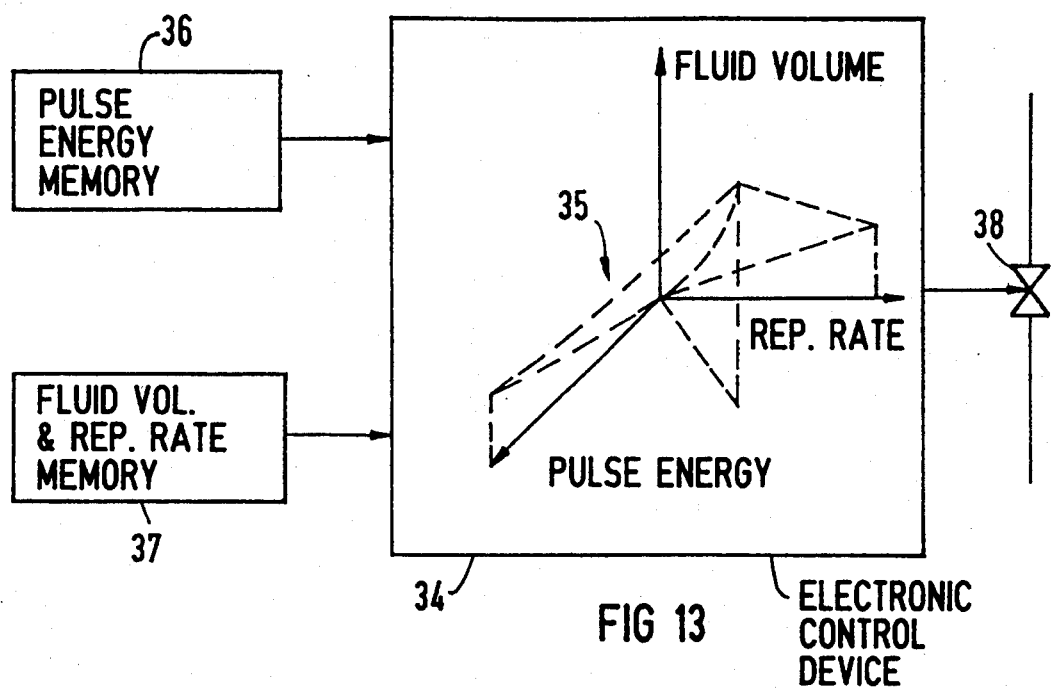
FIG. 13 graphically shows the adaptation of air-to-fluid ratio used in accordance with the principles of the present invention.
Figure 14:
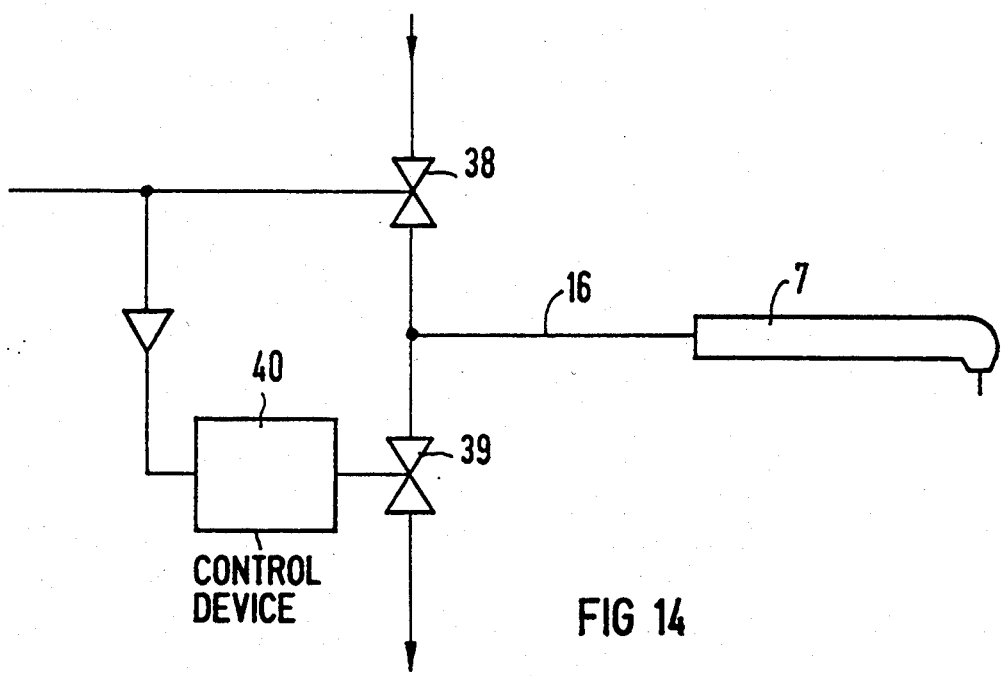
FIG. 14 is a schematic showing of the arrangement of valves for operating the apparatus in accordance with the principles of the present invention.

The adaptation of the air-to-liquid ratio of the aerosol in accordance with the invention is shown in FIG. 13, which also shows means for adjusting the ratio of the liquid proportion to the laser pulse energy and the rate of repetition of the laser pulses. For this purpose, a reference data field 35 is created and stored as a matrix in a PROM or EPROM in an electronic control device 34. Pulse energy data are supplied from a pulse energy memory to the control device 34, and data relating to liquid volume and repetition rate are supplied to the control device 34 from a liquid volume/repetition rate memory 37. The appropriate operating point on the three-dimensional matrix formed in the data field 35 is selected, and is used to control a valve 38 to regulate the liquid volume.

In order to keep the applicator tip 14 as small and easy to handle as possible, in a preferred embodiment the valve 38 is disposed prior to the liquid feed to the applicator tip 14. To avoid the possibility of after flow of the liquid caused by placing the valve 38 so far upstream from the termination of the liquid conduit 16 and by its possible elasticity, phase-displaced low pressure pulses can be applied to the liquid in the liquid conduit 16. As shown in FIG. 14, this can be accomplished by a second valve 39 operated inversely to 38, by a control device 40 preceded by an inverter. Even if the valve 38 is placed closer to the termination of the liquid conduit 16, or if a non-flexible conduit is used, the valve 39 can be used as a pressure relief valve, and the external application of low pressure is then not necessary.

Figure 15:
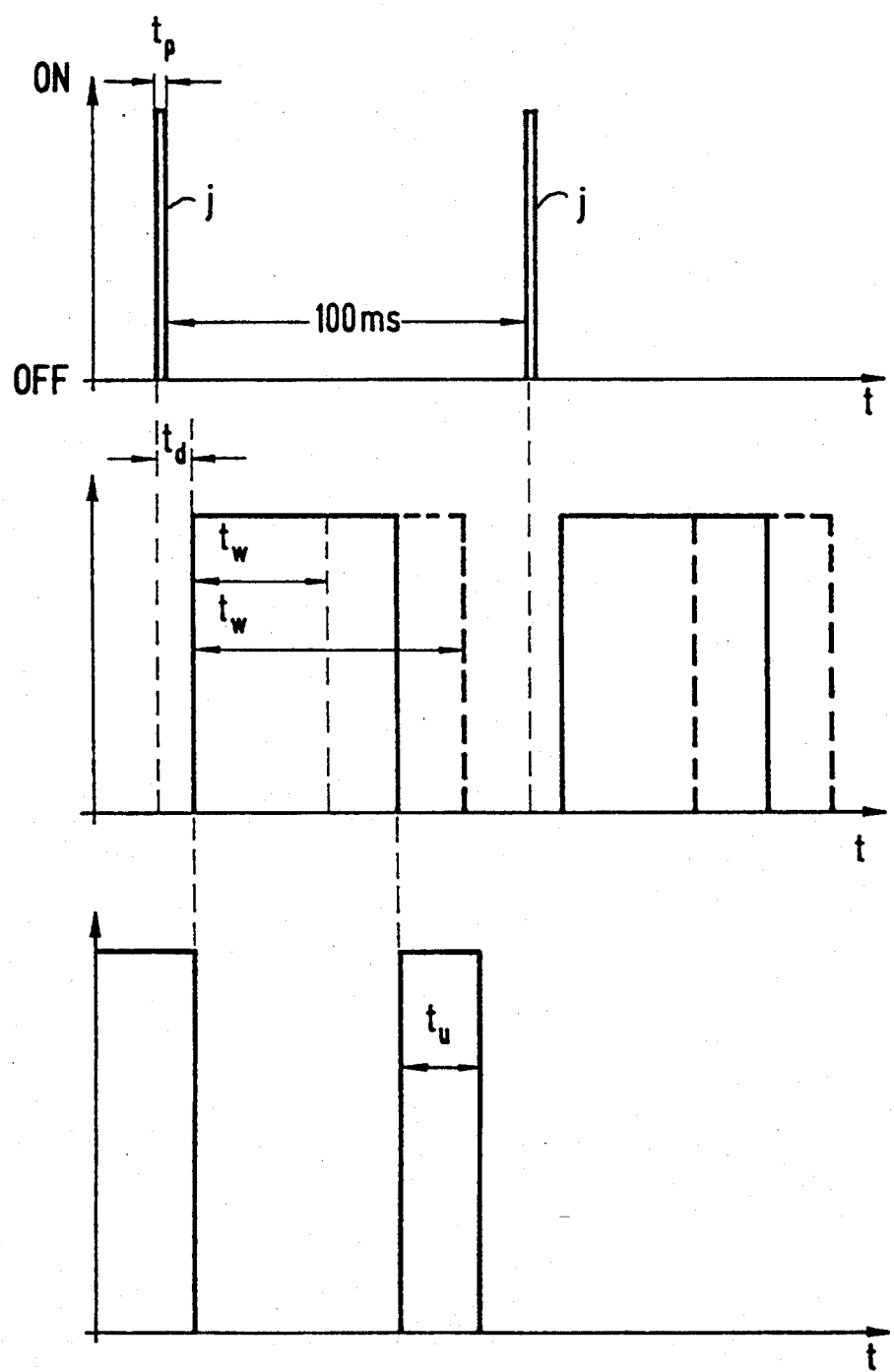
FIG. 15 is a timing diagram for the control of the fluid/air mixture (aerosol) in the operation of the apparatus according to the principles of the present invention.

The timing diagram for controlling the aerosol is shown in FIG. 15. In FIG. 15, the various operating conditions (ON, OFF) for the laser pulses are shown, as well as those for the valve 38 and for the low pressure valve 39. As can be seen in FIG. 15, the liquid valve 38 is controlled phase displaced by a time $t_d$ compared to the leading edge of the laser pulses j. This is for the purpose of keeping the energy losses within the aerosol during the laser pulses as small as possible. The liquid volume is controlled using the pulse-to-pause relationship ($t_w$ $_{min}$ to $t_w$ $_{max}$). The low pressure valve 39 is switched on by a pulse from the control unit 40 for a predetermined time $t_u$, which suffices to reduce the speed of the flow of the liquid in the liquid conduit 16 so that the aerosol is delivered to the operation zone of the laser. The laser pulses are shown as having a duration $t_p$, and having an exemplary pulse pause of 100 ms.

In the preferred embodiment using a pulsed Er:Cr:YSGG laser, the liquid is pure water. Any other liquid may be used, however, in accordance with the principles of the present invention, which is suitable for the particular application, and which has sufficient optical absorption properties at the working wavelength of the laser. At the same time, the use of an optical hollow guide with gas cleansing provides for the protection of the sensitive optical components. Moreover, the advantages of handling ease and sterilization result.

Although modifications and changes may be suggested by those skilled in the art, it is the intention of the inventors to embody within the patent warranted hereon all changes and modifications as reasonably and properly come within the scope of their contribution to the art.

We claim as our invention:

1. An apparatus for ablating hard biological materials, comprising: a pulsed laser which emits pulsed laser radiation in the form of laser pulses each having a time-varying intensity profile and a fundamental frequency having an associated wavelength in a wavelength range selected from the group of wavelength ranges consisting of 200 through 400 rim, 1.3 through 3 microns, and 9.0 through 11 microns, said intensity profile containing intensity spikes which cause generation of harmonics of said fundamental frequency in said pulsed laser radiation;

an optical waveguide which transmits said pulsed laser radiation along a propagation path to a treatment site; and means for coupling said pulsed laser radiation to said optical waveguide including a medium which smooths the intensity profile of said laser pulses with respect to time by removing harmonics in said pulsed laser radiation which exceed a predetermined threshold, and which permits passage of pulsed laser radiation at said fundamental frequency therethrough unchanged.

2. An apparatus as claimed in claim 1 wherein said laser is a solid-state laser.

3. An apparatus as claimed in claim 1 wherein said means for coupling consists of a medium having non-linear optical properties disposed in the propagation path of said pulsed laser radiation for generating harmonics of said fundamental frequency incident on said medium at a power concentration exceeding an average power value for one of said laser pulses.

4. An apparatus as claimed in claim 3 wherein said laser has a resonator and wherein said means for coupling is disposed in said resonator.

5. An apparatus as claimed in claim 2 wherein said laser has a resonator, and wherein said means for coupling is disposed outside of said resonator, and said apparatus further comprisings dichroic beam splitter disposed at an output of said laser which prevents said intensity spikes from passing therethrough.

6. An apparatus as claimed in claim 1 wherein said laser is an Cr:Er:YSGG laser operating at a wavelength of 2.78 microns.

7. An apparatus as claimed in claim 1 wherein said laser is an Er:YAG laser operating at a wavelength of 2.94 microns.

8. An apparatus as claimed in claim 3 wherein said medium is a crystal having a composition selected from the group consisting of lithium-iodate, lithium beta borate, lithium niobate, niobium beta borate, barium beta borate and silver gallium sulfide.

9. An apparatus as claimed in claim 1 wherein said optical waveguide is formed by at least one optical fiber.

10. An apparatus as claimed in claim 9 wherein said at least one optical fiber consists of zirconium fluoride.

11. An apparatus as claimed in claim 9 wherein said optical waveguide further includes an elastomeric inner jacket surrounding said at least one optical fiber and a torsion resistant outer protective jacket surrounding said inner jacket.

12. An apparatus as claimed in claim 1 further comprising a manipulable applicator for directing said pulsed laser radiation onto a treatment site, wherein said optical waveguide is a flexible optical waveguide having a laser-proximate end and an applicator-proximate end and has two rotary quick connectors respectively disposed at said ends for mechanically and optically coupling said laser-proximate end of said flexible optical waveguide to said laser and for optically and mechanically coupling said applicator-proximate end of said flexible optical waveguide to said applicator, each of said rotary quick connectors forming means for preventing torsion forces to be transmitted to said flexible optical waveguide.

13. An apparatus as claimed in claim 9 further comprising a manipulable handpiece optically coupled to said optical waveguide, said handpiece having an applicator endpiece from which said pulsed laser radiation exits onto a treatment site at which said pulsed radiation produced ablation products, said applicator endpiece having surfaces, and said apparatus further comprising means for delivering media into the propagation path of said pulsed laser radiation exiting from said applicator endpiece for preventing said ablation products produced from the treatment site by said pulsed laser radiation from damaging said radiation transmitting surfaces of said applicator endpiece.

14. An apparatus as claimed in claim 13 wherein said applicator endpiece comprises:

an optical hollow guide having an interior channel through which said pulsed laser radiation proceeds to a treatment site; and a gas container, connectable to a source of gas, and in fluid communication with said channel in said optical hollow guide for creating a gas flow through said channel for preventing ablated material from said treatment site from coming into contact with said applicator endpiece.

15. An apparatus as claimed in claim 14 wherein said gas container has a first side through which said pulsed laser radiation enters said gas container and a second side through which said pulsed laser radiation exits said gas container, and said gas container having, at least on said first surface, a window closing said gas container consisting of material transmissive for said pulsed laser radiation.

16. An apparatus as claimed in claim 15 wherein said window consists of mica.

17. An apparatus as claimed in claim 13 wherein said applicator endpiece consists of a solid conical sapphire tip.

18. An apparatus as claimed in claim 13 wherein said means for delivering media is a means for delivering an aerosol consisting of said media.

19. An apparatus as claimed in claim 18 wherein said means for delivering aerosol includes separate means for delivering air and means for delivering fluid and means for mixing said air and fluid to form said aerosol, and means for setting an air-to-fluid ratio and a fluid volume in said aerosol based on the energy and repetition rate of the pulses of said pulsed laser radiation.

* * * * *